United States Patent [19]

Maravetz et al.

[11] Patent Number: 4,818,276
[45] Date of Patent: Apr. 4, 1989

[54] HERBICIDAL 1-ARYL-Δ²-1,2,4-TRIAZOLIN-5-ONES

[75] Inventors: Lester L. Maravetz, Westfield; George Theodoridis, Princeton, both of N.J.

[73] Assignee: FMC Corporation, Philadelphia, Pa.

[21] Appl. No.: 763,855

[22] Filed: Aug. 8, 1985

Related U.S. Application Data

[63] Continuation-in-part of Ser. No. 673,291, Nov. 20, 1984, abandoned, which is a continuation-in-part of Ser. No. 594,602, Mar. 29, 1984, abandoned.

[51] Int. Cl.⁴ .................. A01N 43/64; C07D 249/12
[52] U.S. Cl. ........................................ 71/92; 548/263; 548/265
[58] Field of Search ............... 548/263, 264, 265; 71/92

[56] References Cited

U.S. PATENT DOCUMENTS

| | | | |
|---|---|---|---|
| 4,098,896 | 7/1978 | Edwards | 514/384 |
| 4,213,773 | 7/1980 | Wolf | 71/92 |
| 4,315,767 | 2/1982 | Wolf | 71/91 |
| 4,318,731 | 3/1982 | Kajioka et al. | 548/263 |
| 4,398,943 | 8/1983 | Kajioka et al. | 548/263 |
| 4,404,019 | 9/1983 | Uematsu et al. | 548/265 |
| 4,427,438 | 1/1984 | Nagano et al. | 71/92 |
| 4,431,822 | 2/1984 | Nagano et al. | 548/513 |
| 4,439,229 | 3/1984 | Swithenbank | 71/92 |
| 4,452,981 | 6/1984 | Nagano et al. | 71/92 |

FOREIGN PATENT DOCUMENTS

| | | |
|---|---|---|
| 69855 | 7/1983 | European Pat. Off. . |
| 57-181069 | 2/1982 | Japan . |
| 0157771 | 9/1983 | Japan .................. 548/265 |
| 58-225070 | 12/1983 | Japan . |
| 78-3182 | of 1978 | South Africa . |

OTHER PUBLICATIONS

Nohyaku, "Δ²-1,2,4-Triazolin-5-One, etc.", 12-27-83, CA 100:209881r, (1984).
Nihon Nohyaku, "Herbicidal Delta 2-1,2,4-Triazolin-5-Ones", Chemical Abstracts: C.A., 95:132895s, (1981); abstract of Japanese Kokai 81-32,468, published, 4/1/81.

Primary Examiner—Richard L. Raymond
Assistant Examiner—Patricia L. Morris
Attorney, Agent, or Firm—Robert M. Kennedy; H. Robinson Ertelt; William Schmonsees

[57] ABSTRACT

Novel aryltriazolinone compounds of the formula

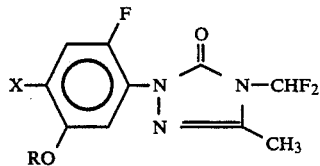

in which X is a chlorine or bromine atom and R is a radical selected from the group consisting of methyl, ethyl, 1-methylethyl, methoxymethyl, 2-methoxyethyl, 1-methyl-2-methoxyethyl, 2-propenyl, 2-propynyl, and 1-methyl-2-propynyl have herbicidal utility against a variety of grassy and broadleaf weeds in both preemergence and postemergence applications and show a selectivity favorable to cotton in preemergence applications.

4 Claims, No Drawings

HERBICIDAL 1-ARYL-Δ²-1,2,4-TRIAZOLIN-5-ONES

This application is a continuation-in-part of U.S. application Ser. No. 673,291, filed Nov. 20, 1984, now abandoned, which is a continuation-in-part of U.S. application Ser. No. 594,602, filed Mar. 29, 1984, now abandoned.

The invention described in this application pertains to weed control in agriculture, horticulture, or other fields where there is a desire to control unwanted plant growth. More specifically, the present application describes novel herbicidal 1-aryl-Δ²-1,2,4-triazolin-5-ones, herbicidal compositions containing the new compounds, methods for preparing the compounds, and methods for preventing or destroying undesired plant growth by preemergence or postemergence application of the herbicidal compositions to the lcous where control is desired. The present compounds may be used to effectively control a variety of both grassy and broadleaf plant species.

Various herbicidal 1-aryl-Δ²-1,2,4-triazolin-5-ones are known in the art. U.S. Pat. No. 4,318,731 and corresponding British Pat. No. 2,056,971 disclose herbicidal aryltriazolinones of the formula

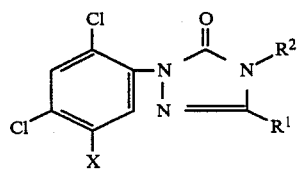

wherein $R^1$ is alkyl, $R^2$ is hydrogen, alkyl, or alkenyl, and X is hydroxy, alkyl, alkoxy, alkoxyalkoxy, alkenyloxy, or alkyloxycarbonylalkyloxy.

British Pat. No. 2,090,250, a continuation-in-part of the above British patent, adds to the above genus compounds wherein $R^2$ is alkynyl, halomethyl, or haloethyl, and X is alkoxy, alkenyloxy, alkynyloxy, alkoxyalkyl, hydroxy, halomethyloxy, or haloethyloxy.

European Patent Application Publication No. 55,105 discloses a series of herbicidal aryltriazolinones of the formula

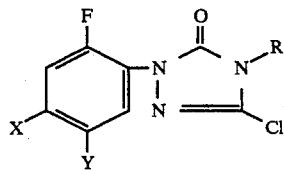

wherein R is alkyl, alkenyl, or cycloalkyl, X is chlorine or bromine, and Y is hydrogen or alkoxy.

Japanese Kokai No. 81-32,468 discloses herbicidal aryltriazolinones of the formula

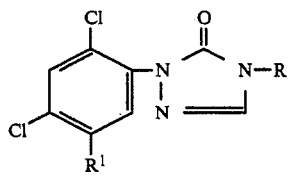

wherein R is hydrogen, alkyl, or 2-propenyl, and $R^1$ is methyl or alkoxy.

South African Patent Application No. 78/3182 discloses herbicidal aryltriazolinones of the formula

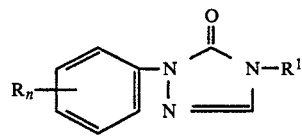

wherein $R_n$ is hydrogen or represents 1 to 4 same or different radicals selected from halogen, nitro, cyano, optionally halo-substituted alkyl, alkoxy, or alkylthio, and optionally substituted phenyl or phenoxy, and $R^1$ is alkyl, alkoxyalkyl, dialkoxyethyl, dialkylaminoethyl, or cycloalkyl.

U.S. Pat. No. 4,315,767 discloses herbicidal bicyclic compounds of the following formula

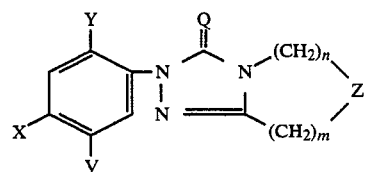

wherein V is hydrogen, halogen, methyl, or alkoxy, X is hydrogen, halogen, cyano, methyl, methoxy, or nitro, Y is hydrogen, halogen, or methyl, m and n are 0 to 4 (m plus n is 2 to 4), Q is oxygen or sulfur, and Z is oxygen, $S(O)_p$, or $NR^1$ wherein p is 0–2 and $R^1$ is alkyl, provided that when m plus n is 2 or 4 then Y and X are other than hydrogen, and when Z is $S(O)_p$ then n is 1 to 4.

Additional herbicidal bicyclic compounds based on the aryltriazolinone nucleus are disclosed in U.S. Pat. No. 4,213,773 and have the following structural formula

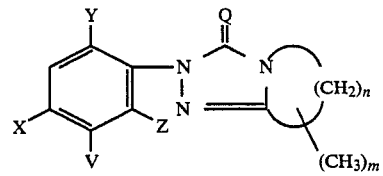

wherein V is hydrogen, halogen, hydroxy, alkyl, or $-OR^1$; $R^1$ is optionally substituted alkyl, cycloalkyl, cycloalkylalkyl, optionally substituted alkenyl, alkynyl, optionally substituted benzyl, alkylaminocarbonyl, (alkyl)(methyl or methoxy)aminocarbonyl, acyl, alkoxycarbonyl, or $-CHR^7R^8$ wherein $R^7$ is hydrogen or alkyl and $R^8$ is cyano, acetyl, hydroxycarbonyl, alkoxycarbonyl, hydroxymethyl, alkoxymethyl, alkylcarbonyloxymethyl, hydroxycarbonylethenyl, alkoxycarbonylethenyl, or a group $-CO-NR^{11}R^{12}$ wherein $R^{11}$ is hydrogen, alkyl, alkenyl, or alkoxy, and $R^{12}$ is hydrogen or alkyl; X is halogen, cyano, methyl, methoxy, or nitro; Y is hydrogen, halogen, or methyl; Z is hydrogen or halogen; n is 3–5; m is 0–2; and Q is oxygen or sulfur, with certain provisos.

A class of Δ²-1,2,4-triazolin-5 ones is disclosed as fungicides in U.S. Pat. No. 4,098,896. The disclosed genus has the formula

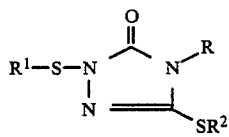

wherein R is alkyl, alkenyl, alkynyl, cycloalkyl, or optionally substituted phenyl or arylalkyl, $R^1$ is haloalkyl or haloalkenyl, and $R^2$ is optionally substituted alkyl, alkenyl, or alkynyl, or optionally substituted aryl, arylalkyl, or alkylaryl.

The compounds of this invention are 1-[4-halo-2-fluoro-5-(substituted)oxyphenyl]-3-methyl-4-difluoromethyl-$\Delta^2$-1,2,4-triazolin-5-ones of the formula

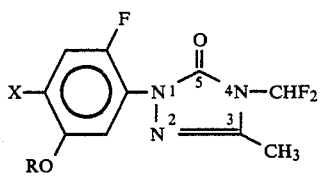

wherein X is chlorine or bromine and R is alkyl, alkenyl, alkynyl, alkoxyalkyl, or alkyl-S(O)$_n$-alkyl wherein n is 0 to 2.

The present compounds are named in accordance with the numbering system shown in formula I, for the ring atoms of the heterocycle which is the same as the numbering system used in U.S. Pat. No. 4,318,731, supra, for smilar compounds.

A preferred subgenus of this invention comprises the compounds of formula I in which R is selected from —CH$_3$, —C$_2$H$_5$, —CH(CH$_3$)$_2$, —CH$_2$OCH$_3$, —CH$_2$CH$_2$OCH$_3$, —CH(CH$_3$)CH$_2$OCH$_3$, —CH$_2$CH=CH$_2$, —CH$_2$C≡CH, and —CH(CH$_3$)C≡CH.

One aspect of the present invention pertains to the compounds of formula I in which X is a chlorine atom. A preferred subgenus of this aspect of the invention comprises the compounds in which R is selected from —CH(CH$_3$)$_2$, —CH$_2$OCH$_3$, —CH(CH$_3$)CH$_2$OCH$_3$, —CH$_2$CH=CH$_2$, —CH$_2$C≡CH, and —CH(CH$_3$)C≡CH. The compounds of the subgenus, particularly where R is —CH(CH$_3$)$_2$, —CH$_2$OCH$_3$, —CH$_2$CH=CH$_2$, —CH$_2$C≡CH, or —CH(CH$_3$)C≡CH, show a selectivity favorable to cotton in preemergence applications at application rates which inhibit or control emergence or growth of a variety of weeds. Specific embodiments giving good weed control at low preemergence application rates and showing a selectivity favorable to cotton include the species in which R is variously —CH(CH$_3$)$_2$, —CH$_2$OCH$_3$, and —CH$_2$C≡CH. R is advantageously —CH$_2$OCH$_3$ or —CH$_2$C≡CH.

The compounds of formula I in which X is a bromine atom form a second, preferred aspect of the present invention. The presence of a bromine atom at the C-4 position of the phenyl ring in formula I was found to generally give superior cotton selectivity in preemergence applications at application rates at which a variety of weeds are controlled. A preferred subgenus of this aspect of the invention comprises the compounds in which R is selected from —CH$_3$, —C$_2$H$_5$, —CH(CH$_3$)$_2$, —CH$_2$OCH$_3$, —CH$_2$CH$_2$OCH$_3$, —CH$_2$C≡CH, and —CH(CH$_3$)C≡CH. In a preferred specific embodiment, R is selected from —CH$_3$, —CH$_2$OCH$_3$, and —CH$_2$C≡CH.

The present compounds, which have a fluorine atom at the C-2 position of the phenyl ring, in general have herbicidal properties far superior to those of the corresponding compounds having a chlorine atom at C-2 of the phenyl ring, and are highly active at low application rates against a variety of grassy and broadleaf weed species in both preemergence and postemergence applications.

The compounds of this invention may be prepared by methods analogous to the methods described in the references above for similar compounds or by methods within the skill of the art. The disclosures in the above references pertaining to methods of preparation are incorporated herein by reference. A method of preparation exemplified herein is illustrated in the following chemical equations for the compound of formula I in which X is Cl and R is —CH$_2$C≡CH.

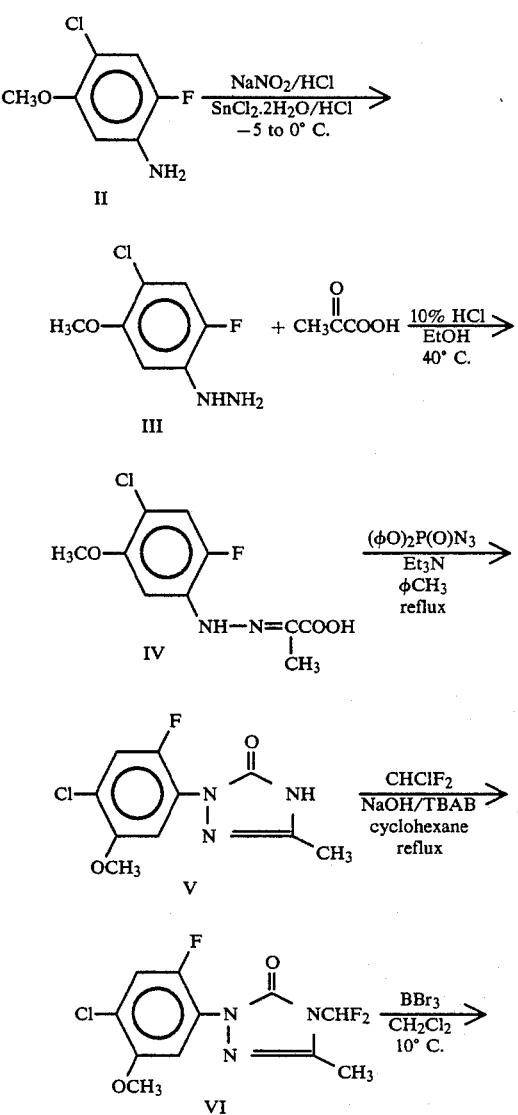

-continued

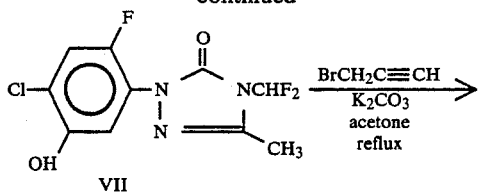

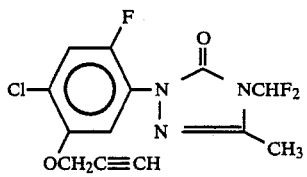

4-Chloro-2-fluoro-5-methoxyaniline, compound II, was prepared in five steps from commercially available 2-chloro-4-fluorophenol in the manner described by E. Nagano et al. in European Patent Application Publication No. 69,855, published Jan. 19, 1983, incorporated herein by reference. Compound II was converted to the corresponding hydrazine III by diazotization followed by reduction of the diazonium salt with stannous chloride. Treatment of the arylhydrazine with pyruvic acid in the presence of 10% hydrochloric acid and ethanol gave the arylhydrazone IV which upon treatment with diphenylphosphoryl azide afforded the aryltriazolinone V. Compound V was converted to the final product in three steps by methods analogous to those disclosed in British Pat. No. 2,090,250 for similar compounds. Alkylation of Compound V with chlorodifluoromethane produced the N-difluoromethyl derivative VI which was demethylated at the ether linkage upon treatment with boron tribromide in methylene chloride to give the corresponding phenol VII. Alkylation of the 5-hydroxyphenyl compound with propargyl bromide in the presence of potassium carbonate and acetone produced the present compound.

Preparation of the present compounds and the intermediate compounds shown in the chemical equations above is illustrated further in the following examples. All temperatures shown are in degrees Celcius, and reduced pressures for concentration of liquid were produced by a vacuum pump.

EXAMPLE 1

Preparation of Intermediates

A. 4-Chloro-2-fluoro-5-methoxyphenylhydrazine

A stirred solution of 48.0 g (0.27 mole) of 4-chloro-2-fluoro-5-methoxyaniline in 50 mL of concentrated hydrochloric acid was cooled to −5° C., and 23.5 g (0.34 mole) of sodium nitrite in 100 mL of water was added dropwise. Upon complete addition, the reaction mixture was stirred at 0° C. for one hour. A solution of 154.0 g (0.68 mole) of stannous chloride in 225 mL of concentrated hydrochloric acid was cooled to 0° C., and the cold solution prepared above was slowly added to it. Upon complete addition, the reaction mixture was allowed to warm to ambient temperature, then was filtered to collect a solid. The solid was made basic and extracted with toluene. The toluene layer was separated and dried over magnesium sulfate, then filtered. The filtrate was concentrated under reduced pressure to give 22.4 g of 4-chloro-2-fluoro-5-methoxyphenylhdrazine as a solid.

The nmr spectrum was consistent with the proposed structure.

B. Pyruvic acid, 4-chloro-2-fluoro-5-methoxyphenylhydrazone

A stirred solution of 21.0 g (0.11 mole) of 4-chloro-2-fluoro-5-methoxyphenylhydrazine and 100 mL of aqueous 10% hydrochloric acid in 100 mL of ethanol was warmed to 40° C., and a solution of 10.0 g (0.114 mole) of pyruvic acid in 20 mL of water was added. Upon complete addition, the reaction mixture was stirred for one hour. An additional 50 mL of water was added, and the reaction mixture was filtered to collect a solid. The solid was air dried to give 29.0 g of pyruvic acid, 4-chloro-2-fluoro-5-methoxyphenylhydrazone; mp 166°–169° C.

The nmr spectrum was consistent with the proposed structure.

C. 1-(4-Chloro-2-fluoro-5-methoxyphenyl)-3-methyl-$\Delta^2$-1,2,4-triazolin-5-one A stirred solution of 27.0 g (0.104 mole) of pyruvic acid, 4-chloro-2-fluoro-5-methoxyphenylhydrazone, 29.0 g (0.105 mole) of diphenylphosphoryl azide, and 11.0 g (0.108 mole) of triethylamine in 500 mL of toluene was heated under reflux for four hours. The reaction mixture was cooled to ambient temperature and extracted with aqueous 10% sodium hydroxide. The aqueous layer was separated and neutralized with gaseous carbon dioxide, and a solid was collected by filtration. The solid was air dried to give 11.0 g of 1-(4-chloro-2-fluoro-5-methoxyphenyl)-3-methyl-$\Delta^2$-1,2,4-triazolin-5-one; mp 193°–195° C.

The nmr spectrum was consistent with the proposed structure.

D. 1-(4-Chloro-2-fluoro-5-methoxyphenyl)-3-methyl-4-difluoromethyl-$\Delta^2$-1,2,4-triazolin-5-one A stirred mixture of 10.0 g (0.039 mole) of 1-(4-chloro-2-fluoro-5-methoxyphenyl)-3-methyl-$\Delta^2$-1,2,4-triazolin-5-one, 10.0 g (0.031 mole) of tetrabutylammonium bromide, and 10.0 g (0.25 mole) of sodium hydroxide in 250 mL of cyclohexane was warmed to 60° C., and 10.0 g (0.116 mole) of chlorodifluoromethane was bubbled into the reaction mixture. Upon complete addition, the reaction mixture was warmed to reflux temperature and stirred for one hour. The hot solution was decanted from a pot residue and was allowed to cool to ambient temperature. Methylene chloride was added to the cooled mixture to dissolve a solid precipitate, and the whole was washed with aqueous 10% hydrochloric acid, then with aqueous 10% sodium hydroxide. The organic layer was separated and dried over magnesium sulfate, then filtered. The filtrate was concentrated under reduced pressure to give 5.0 g of 1-(4-chloro-2-fluoro-5-methoxyphenyl)-3-methyl-4-difluoromethyl-$\Delta^2$-1,2,4-triazolin-5-one; mp 86°–88° C.

The nmr spectrum was consistent with the proposed structure.

E. 1-(4-Chloro-2-fluoro-5-hydroxyphenyl)-3-methyl-4-difluoromethyl-$\Delta^2$-1,2,4-triazolin-5-one A stirred solution of 4.6 g (0.015 mole) of 1-(4-chloro-2-fluoro-5-methoxyphenyl)-3-methyl-4-difluoromethyl-$\Delta^2$-1,2,4-triazoline-5-one in 200 mL of methylene chloride was cooled to 10° C., and a solution of 11.2 g (0.045 mole) of boron tribromide in 45 mL of methylene chloride was added. Upon complete addition, the cooling bath was removed, and the reaction mixture was stirred for four hours, as it warmed to ambient temperature. Water (100 mL) was added and stirring was continued for an additional 18 hours. The organic layer was separated, dried over magnesium sulfate, and filtered. The filtrate was concentrated under reduced pressure to give 4.4 g of 1-(4-chloro-2-fluoro-5-hydroxyphenyl-3-methyl-4-difluoromethyl-$\Delta^2$-1,2,4-triazolin-5-one; mp 147°-152° C.

The nmr spectrum was consistent with the proposed structure.

EXAMPLE 2

Preparation of 1-(4-Chloro-2-Fluoro-5-Propargyloxyphenyl)-3-Methyl-4-Difluoromethyl-$\Delta^2$-1,2,4-Triazolin-5-One To a stirred mixture of 0.7 g (0.0023 mole) of 1-(4-chloro-2-fluoro-5-hydroxyphenyl)-3-methyl-4-difluoromethyl-$\Delta^2$-1,2,4-triazolin-5-one and 0.2 g (0.0015 mole) of potassium carbonate in 50 mL of acetone was added 0.3 g (0.0025 mole) of propargyl bromide. Upon complete addition, the reaction mixture was heated at reflux for three hours, then concentrated under reduced pressure. The residue was dissolved in methylene chloride and washed with water and aqueous 10% sodium hydroxide. The organic layer was dried over magnesium sulfate and filtered. The filtrate was concentrated under reduced pressure to give 0.33 g of 1-(4-chloro-2-fluoro-5-propargyloxyphenyl)-3-methyl-4-difluoromethyl-$\Delta^2$-1,2,4-triazolin-5-one as an oil. A sample of this material was employed in the herbicidal efficacy tests described below.

The nmr spectrum was consistent with the proposed structure.

The reaction above was repeated with a purer sample of 1-(4-chloro-2-fluoro-5-hydroxyphenyl)-3-methyl-4-difluoromethyl-$\Delta^2$-1,2,4-triazolin-5-one (mp 158°-162° C.) to give the desired propargyloxy derivative as a solid, mp 75°-78° C.

The nmr spectrum was consistent with the proposed structure.

A sample of product prepared in a similar manner was purified for microanalysis, mp 82°-85° C.

Analysis calc'd for $C_{13}H_9ClF_3N_3O_2$: C 47.07, H 2.73, N 12.67; Found: C 46.86, H 2.47, N 12.48.

EXAMPLE 3

Preparation of 1-[4-Chloro-2-Fluoro-5-(1-Methylethoxy)Phenyl]-3-Methyl-4-Difluoromethyl-$\Delta^2$-1,2,4-Triazolin-5-One This compound was prepared in a manner analogous to Example 2 using 0.50 g (0.0017 mole) of 1-(4-chloro-2-fluoro-5-hydroxyphenyl)-3-methyl-4-difluoromethyl-$\Delta^2$-1,2,4-triazolin-5-one, 0.36 g (0.0021 mole) of 2-iodopropane, and 0.71 g (0.0051 mole) of potassium carbonate in 50 mL of acetone. The yield of 1-[4-chloro-2-fluoro-5-(1-methylethoxy)phenyl]-3-methyl-4-difluoromethyl-$\Delta^2$-1,2,4-triazolin-5-one was 0.40 g; m.p. 77°-79° C.

The nmr spectrum was consistent with the proposed structure.

EXAMPLE 4

Preparation of 1-[4-Chloro-2-Fluoro-5-(1-Methyl-2-Propynyloxy)-Phenyl]-3-Methyl-4-Difluoromethyl-$\Delta^2$-1,2,4-Triazolin-5-One This compound was prepared in a manner analogous to Example 2 using 0.50 g (0.0017 mole) of 1-(4-chloro-2-fluoro-5-hydroxyphenyl)-3-methyl-4-difluoromethyl-$\Delta^2$-1,2,4-triazolin-5-one, 0.28 g (0.0021 mole) of 3-bromo-1-butyne, and 0.36 g (0.0021 mole) of potassium carbonate in 50 mL of acetone. The yield of 1-[4-chloro-2-fluoro-5-(1-methyl-2-propynyloxy)phenyl]-3-methyl-4-difluoromethyl-$\Delta^2$-1,2,4-triazolin-5-one, as an oil, was 0.35 g.

The nmr spectrum was consistent with the proposed structure.

Analysis calc'd for $C_{14}H_{11}ClF_3N_3O_2$: C 48.64, H 3.21, N 12.15; Found: C 48.39, H 3.32, N 11.95.

EXAMPLE 5

Preparation of 1-(4-Chloro-2-Fluoro-5-Methoxymethoxyphenyl)-3-Methyl-4-Difluoromethyl-$\Delta^2$-1,2,4-Triazolin-5-One This compound was prepared in the manner of Example 2 using 0.75 g (0.0026 mole) of 1-(4-chloro-2-fluoro-5-hydroxyphenyl)-3-methyl-4-difluoromethyl-$\Delta^2$-1,2,4-triazolin-5-one, 0.21 g (0.026 mole) of chloromethyl methyl ether, and 0.35 g (0.0026 mole) of potassium carbonate in 60 mL of acetone. The yield of 1-[4-chloro-2-fluoro-5-methoxymethoxyphenyl]-3-methyl-4-difluoromethyl-$\Delta^2$-1,2,4-triazolin-5-one, as an oil, was 0.84 g.

The nmr spectrum was consistent with the proposed structure.

Analysis calc'd for $C_{12}H_{11}ClF_3N_3O_3$: C 42.68, H 3.28, N 12.44; Found: C 42.59; H 3.42, N 12.33.

EXAMPLE 6

Preparation of 1-(4-Chloro-2-Fluoro-5-Allyloxyphenyl)-3-Methyl-4-Difluoromethyl-$\Delta^2$-1,2,4-Triazolin-5-One This compound was prepared in the manner of Example 2 using 0.75 g (0.0026 mole) of 1-(4-chloro-2-fluoro-5-hydroxyphenyl)-3-methyl-4-difluoromethyl-$\Delta^2$-1,2,4-triazolin-5-one, 0.31 g (0.0026 mole) of allyl bromide, and 0.35 g (0.0026 mole) of potassium carbonate in 60 mL of acetone. The yield of 1-(4-chloro-2-fluoro-5-allyloxyphenyl)-3-methyl-4-difluoromethyl-$\Delta^2$-1,2,4-triazolin-5-one was 0.85 g; m.p. 53°-55° C.

The nmr spectrum was consistent with the proposed structure.

Analysis calc'd for $C_{13}H_{11}ClF_3N_3O_2$: C 46.64, H 3.21, N 12.45; Found: C 46.79, H 3.32, N 12.59.

EXAMPLE 7

Preparation of 1-[4-Chloro-2-Fluoro-5-(1-Methyl-2-Methoxyethoxy)-Phenyl]-3-Methyl-4-Difluoromethyl-$\Delta^2$-1,2,4-Triazolin-5-one A stirred mixture of 0.45 g (0.0015 mole) of 1-(4-chloro-2-fluoro-5-hydroxyphenyl)-3-methyl-4-difluoromethyl-$\Delta^2$-1,2,4-triazolin-5-one and 0.41 g (0.0017 mole) of sodium hydride in 8 mL of dimethylformamide was warmed to 90° C. The reaction was cooled to 40° C., and 0.37 g (0.0015 mole) of the tosylate of methoxypropan-2-ol was added in one portion. The reaction mixture was heated at temperatures varying from 40° to 140° C., then was allowed to cool to ambient temperature and was stirred for 16 hours. The reaction mixture was partitioned between water and methylene chloride. The methylene chloride layer was washed sequentially with aqueous 10% sodium hydroxide, aqueous 10% hydrochloric acid, and water. The organic layer was dried with magnesium sulfate and filtered. The filtrate was concentrated under reduced pressure to give 0.38 g of 1-[4-chloro-2-fluoro-5-(1-methyl-2-methoxyethoxy)phenyl]-3-methyl-4-difluoromethyl-$\Delta^2$-1,2,4-triazolin-5-one as an oil.

The nmr spectrum was consistent with the proposed structure.

EXAMPLE 8

Preparation of 1-(4-Bromo-2-Fluoro-5-Methoxyphenyl)-3-Methyl-4-Difluoromethyl-$\Delta^2$-1,2,4-Triazolin-5-One

Step A. 2-Bromo-4-fluorophenyl methyl carbonate

A stirred solution of 561 g (5.0 moles) of 4-fluorophenol in 600 mL of dioxane was cooled in an ice-water bath and 831 g (5.2 moles) of bromine was added dropwise. The complete addition required 1.5 hours, during which the reaction mixture temperature was maintained at 14°-25° C. Following the addition, the ice-water bath was removed, and the reaction mixture temperature rose to 35° C. The reaction mixture was stirred for two hours, then 600 mL of water, followed by 420 mL of 10.8N aqueous sodium hydroxide were added dropwise over 30 minutes and 1 hour respectively. Upon complete addition, the reaction mixture was cooled to 0°-10° C., and 591 g (6.15 moles) of methyl chloroformate was added dropwise over four hours. Upon complete addition, the reaction mixture was allowed to warm to ambient temperature and was stirred for 17 hours. After this time, 450 g of aqueous 50% sodium hydroxide was added to neutralize the reaction mixture. The resultant solid was collected by filtration, and the filter cake washed with two 500 mL portions of water. The solid was dried under reduced pressure to give 1211 g of 2-bromo-4-fluorophenyl methyl carbonate; m.p. 75°-78° C.

The nmr spectrum was consistent with the proposed structure.

Step B. 2-Bromo-4-fluoro-5-nitrophenyl methyl carbonate

A rapidly stirred solution of 946 g (3.8 moles) of 2-bromo-4-fluorophenyl methyl carbonate in 1292 mL of sulfuric acid was cooled to 5°-10° C., and 368 g (4.18 moles) of 70% nitric acid was added dropwise over two hours. Upon complete addition, the reaction mixture was allowed to warm to ambient temperature and was stirred for two hours. The reaction mixture was poured into 5000 mL of ice water. Any material remaining in the reaction vessel was washed into the ice-water with 750 mL of water. The resultant solid was collected by filtration and washed with 1000 mL of water. The solid was dried with mild heat under reduced pressure to give 1031 g of 2-bromo-4-fluoro-5nitrophenyl methyl carbonate.

The nmr spectrum was consistent with the proposed structure.

Step C. 2-Bromo-4-fluoro-5-nitrophenol

A stirred solution of 1031 g (3.5 moles) of 2-bromo-4-fluoro-5-nitrophenyl methyl carbonate in 300 mL of 2.3N aqueous sodium hydroxide was heated to reflux and stirred for three hours. The hot reaction mixture was filtered through diatomaceous earth. Any material remaining in the reaction vessel was washed onto the filter cake with 1000 mL of water. The filtrate was cooled to 8°-10° C., and 560 mL of concentrated hydrochloric acid was added, with stirring, over one hour. The resultant solid was collected by filtration. Any material remaining in the reaction vessel was washed onto the filter cake with 1000 mL of water. The dried filter cake was recrystallized from toluene to give, in two crops, 543 g of 2-bromo-4-fluoro-5-nitrophenol, m.p. 124°-126° C.

The nmr spectrum were consistent with the proposed structure.

Step D. 4-Bromo-2-fluoro-5-methoxynitrobenzene

A stirred solution of 30.0 g (0.127 mole) of 2-bromo-4-fluoro-5-nitrophenol, 26.9 g (0.19 mole) of methyl iodide, and 26.3 g (0.19 mole) of potassium carbonate in 200 mL of acetone was heated at reflux for five hours. The reaction mixture was filtered, and the filtrate concentrated under reduced pressure to give a residue. The residue was dissolved in methylene chloride and passed through a column of silica gel. The elute was concentrated under reduced pressure to give 30 g of 4-bromo-2-fluoro-5-methoxynitrobenzene; m.p. 74°-76° C.

Step E. 4-Bromo-2-fluoro-5-methoxyaniline

To a stirred solution of 30.0 g (0.12 mole) of 4-bromo-2-fluoro-5-methoxynitrobenzene in 200 mL of acetic acid was added 40 mL of water, followed by the portionwise addition of 30.0 g (0.54 mole) of iron filings during a 2.5 hour period. Upon complete addition, the reaction mixture was stirred at 25°-35° C. for one hour. Diethyl ether, 200 mL, was added, and the reaction mixture was filtered through a pad of diatomaceous earth. The filtrate was washed with 200 mL of water. The organic layer was separated and neutralized with solid sodium bicarbonate. The mixture was dried with magnesium sulfate and filtered. The filtrate was concentrated under reduced pressure to give a residual solid. The solid was recrystallized from petroleum ether to give 23.5 g of 4-bromo-2-fluoro-5-methoxyaniline; m.p. 60°-62° C.

Step F. Pyruvic acid, 4-bromo-2-fluoro-5-methoxyphenylhdrazone

Under a nitrogen atmosphere, a stirred solution of 23.5 g (0.107 mole) of 4-bromo-2-fluoro-5-methoxyaniline in 150 mL of concentrated hydrochloric acid was cooled to −9° C., and a solution of 7.4 g (0.107 mole) of sodium nitrite in 40 mL of water was added dropwise over two hours. Upon complete addition, the reaction mixture was stirred at −9° C. for 45 minutes, then a solution of 36.0 g (0.160 mole) of stannous chloride in 50 mL of concentrated hydrochloric acid was added dropwise over one hour. The reaction mixture temperature was maintained at −9° to 0° C. throughout the addition. Upon complete addition, the reaction mixture was allowed to warm to ambient temperature and was stirred for two hours. After this time, 100 mL of water was added to the reaction mixture, followed by the dropwise addition of a solution of 9.4 g (0.107 mole) of pyruvic acid in 100 mL of water. Upon complete addition, the reaction mixture was stirred for 30 minutes at ambient temperature. The reaction mixture was filtered to collect a solid. The solid was dried to give 23.5 g of pyruvic acid, 4-bromo-2-fluoro-5-methoxyphenylhydrazone; m.p. 156°–158° C.

Step G.
1-(4-Bromo-2-fluoro-5-methoxyphenyl)-3-methyl-$\Delta^2$-1,2,4-triazolin-5-one A stirred solution of 22.7 g (0.074 mole) of pyruvic acid, 4-bromo-2-fluoro-5-methoxyphenylhydrazone, 20.5 g (0.074 mole) of diphenylphosphoryl azide, and 7.5 g (0.074 mole) of triethylamine in 150 mL of toluene was heated at a reflux for four hours. The reaction mixture was cooled and diluted with diethyl ether. The mixture was extracted three times with aqueous 1 molar sodium hydroxide. The combined extracts were washed with diethyl ether and made acidic with concentrated hydrochloric acid. The resultant solid was collected by filtration and washed with water. The solid was dried to give 15.0 g of 1-(4-bromo-2-fluoro-5-methoxyphenyl)-3-methyl-$\Delta^2$-1,2,4-triazolin-5-one.

The nmr spectrum was consistent with the proposed structure.

H.
1-(4-Bromo-2-fluoro-5-methoxyphenyl)-3-methyl-4-difluoromethyl-$\Delta^2$-1,2,4-triazolin-5-one A stirred solution of 15.0 g (0.050 mole) of 1-(4-bromo-2-fluoro-5-methoxyphenyl)-3-methyl-$\Delta^2$-1,2,4-triazolin-5-one, 5.6 g (0.10 mole) of potassium hydroxide, and 1.6 g (0.005 mole) of tetrabutylammonium bromide in 150 mL of tetrahydrofuran was saturated with gaseous chlorodifluoromethane. The reaction mixture was stirred at ambient temperature for 16 hours. An additional 2.9 g (0.052 mole) of potassium hydroxide was added, and the reaction mixture was again saturated with chlorodifluoromethane. Upon complete saturation, the reaction mixture was stirred for two hours, then diluted with diethyl ether. The mixture was washed with water, then with aqueous saturated sodium chloride. The organic layer was dried with sodium sulfate, filtered, and the filtrate concentrated under reduced pressure to give a residue. The residue was subjected to column chromatography on silica gel. Elution was accomplished with 2:1 methylene chloride:petroleum ether. The appropriate fractions were combined and concentrated under reduced pressure to give 4.2 g of 1-(4-bromo-2-fluoro-5-methoxyphenyl)-3-methyl-4-difluoromethyl-$\Delta^2$-1,2,4-triazolin-5-one; m.p. 129°–130° C.

The nmr and the ir spectra were consistent with the proposed structure.

Analysis calc'd for $C_{11}H_9BrF_3N_3O_2$: C 37.52, H 2.58, N 11.93; Found: C 37.38, H 2.35, N 11.52.

EXAMPLE 9

Preparation of 1-(4-Bromo-2-Fluoro-5-Methoxymethoxyphenyl)-3-Methyl-4-Difluoromethyl-$\Delta^2$-1,2,4-Triazolin-5-One Step A.
1-(4-Bromo-2-fluoro-5-hydroxyphenyl)-3-methyl-4-difluoromethyl-$\Delta^2$-1,2,4-triazolin-5-one A stirred solution of 7.3 g (0.029 mole) of boron tribromide in 30 mL of methylene chloride was cooled to −40° C., and a solution of 3.0 g (0.009 mole) of 1-(4-bromo-2-fluoro-5-methoxyphenyl)-3-methyl-4-difluoromethyl-$\Delta^2$-1,2,4-triazolin-5-one (Example 8) in 25 mL of methylene chloride was added dropwise. The reaction mixture temperature was maintained at −40° C. throughout the addition. Upon complete addition, the reaction mixture was allowed to warm to ambient temperature and was stirred for 16 hours. The reaction mixture was poured into ice-water, and the mixture extracted with diethyl ether. The extract was dried with sodium sulfate, filtered, and the filtrate concentrated under reduced pressure to give a residue. The residue was dissolved in diethyl ether, and the solution was passed through a pad of silica gel. The eluate was concentrated under reduced pressure to give 2.9 g of 1-(4-bromo-2-fluoro-5-hydroxyphenyl)-3-methyl-4-difluoromethyl-$\Delta^2$-1,2,4-triazolin-5-one.

The nmr and the ir spectra were consistent with the proposed structure.

The nmr and the ir spectra were consistent with the proposed structure.

Step B.
1-(4-2-fluoro-5-methoxymethoxyphenyl)-3-methyl-4-difluoromethyl-$\Delta^2$-1,2,4-triazolin-5-one To a stirred suspension of 0.15 g (0.003 mole) of sodium hydride (50% in mineral oil) in 10 mL of toluene was slowly added 1.1 g (0.003 mole) of 1-(4-bromo-2-fluoro-5-hydroxyphenyl)-3-methyl-4-difluoromethyl-$\Delta^2$-1,2,4-triazolin-5-one. N,N-dimethylacetamide (1–2 mL) was added and the reaction mixture was stirred at ambient temperature until it became clear. The reaction was cooled to 20° C., and 0.8 g (0.006 mole) of methoxymethyl bromide was added. Upon complete addition, the reaction mixture was stirred at ambient temperature for 16 hours. The reaction mixture was poured onto ice and allowed to stand for one hour. The organic layer was separated and dried with magnesium sulfate. The mixture was filtered, and the filtrate subjected to column chromatography on silica gel. Elution was accomplished with 4:1 methylene chloride:heptane. The appropriate fractions were combined and concentrated under reduced pressure to give 0.9 g of 1-(4-bromo-2-fluoro-5-methoxymethoxyphenyl)-3-methyl-4-difluoromethyl-$\Delta^2$-1,2,4-triazolin-5-one as an oil.

The nmr spectrum was consistent with the proposed structure.

Analysis calc'd for $C_{11}H_{12}BrF_3N_3O_3$: C 37.72, H 2.89, N 10.99; Found: C 38.32, H 2.86, N 10.91.

EXAMPLE 10

Preparation of 1-(4-Bromo-2-Fluoro-5-Propargyloxyphenyl)-3-Methyl-4-Difluoromethyl-$\Delta^2$-1,2,4-Triazolin-5-One A stirred solution of 2.5 g (0.008 mole) of 1-(4-bromo-2-fluoro-5-hydroxyphenyl)-3-methyl-4-difluoromethyl-$\Delta^2$-1,2,4-triazolin-5-one (prepared as in Step A, Example 9), 1.6 g (0.012 mole) of potassium carbonate, and 1.9 g (0.017 mole) of propargyl bromide in 30 mL of acetone was heated at reflux for 16 hours. The reaction mixture was cooled and concentrated under reduced pressure to give a residue. The residue was dissolved in methylene chloride and subjected to column chromatography on silica gel. Elution was accomplished using methylene chloride. The appropriate fractions were combined and concetrated under reduced pressure to give 2.3 g of 1-(4-bromo-2-fluoro-5-propargyloxyphenyl)-3-methyl-4-difluoromethyl-Δ²-1,2,4-triazolin-5-one; m.p. 70°-72° C.

The nmr spectrum was consistent with the proposed structure.

Analysis calc'd for $C_{13}H_9BrF_3N_3O_2$: C 41.51, H 2.41, N 11.17; Found: C 41.33, H 2.19, N 11.35.

the following compounds were prepared from 1-(4-bromo-2-fluoro-5-hydroxyphenyl)-3-methyl-4-difluoromethyl-Δ²-1,2,4-triazolin-5-one (Example 9A) by an alkylation procedure analogous to that described above in either Example 9B or Example 10:

EXAMPLE 11

1-(4-bromo-2-fluoro-5-ethoxyphenyl)-3-methyl-4-difluoromethyl-Δ²-1,2,4-triazolin-5-one, m.p. 106°-108° C. The ir and nmr spectra were consistent with the proposed structure.

Analysis calc'd for $C_{12}H_{11}BrF_3N_3O_2$: C 39.36, H 3.03, N 11.48; Found: C 39.65, H 2.82, N 11.22.

EXAMPLE 12

1-[4-bromo-2-fluoro-5-(1-methylethoxy)-phenyl]-3-methyl-4-difluoromethyl-Δ²-1,2,4-triazolin-5-one, obtained as an oil. The ir and nmr spectra were consistent with the proosed structure.

Analysis calc'd for $C_{13}H_{13}BrF_3N_3O_2$: C 41.07, H 3.45, N 11.05; Found: C 41.03, H 3.19, N 10.93.

EXAMPLE 13

1-[4-bromo-2-fluoro-5-(1-methyl-propargyloxy)-phenyl]-3-methyl-4-difluoromethyl-Δ²-1,2,4-triazolin-5-one, m.p. 80°-82° C. The ir and nmr spectra were consistent with the proposed structure.

Analysis calc'd for $C_{14}H_{11}BrF_3N_3O_2$: C 43.10, H 2.84, N 10.76; Found: C 43.32, H 2.83, N 10.54.

EXAMPLE 14

1-[4-bromo-2-fluoro--5-(2-methoxyethoxy)phenyl]-3-methyl-4-difluoromethyl-Δ²-1,2,4-triazolin-5-one, m.p. 81°-82° C. The ir and nmr spectra were consistent with the proposed structure.

Anaysis calc'd for $C_{13}H_{13}BrF_3N_3O_3$: C 39.41, H 3.31, N 10.61; Found: C 39.25, H 3.08, N 10.31.

Herbicidal Activity

Comparative herbicidal efficacy data are given in Tables 1-5 below for the present compound of Example 2 and the 2-chloro analog of that compound. The 2-chloro compound is 1-(2,4-dichloro-5-propargyloxyphenyl)-3-methyl-4-difluoromethyl-Δ²-1,2,4-triazolin-5-one and is disclosed in British Pat. No. 2,090,250, supra. While the present compound of Example 2 differs structurally from the known compound only in having a fluorine atom instead of chlorine at the C-2 position of the phenyl ring, it was markedly and unexpectedly more active than the prior compound against a variety of broadleaf plant species in both preemergence and postemergence applications in side-by-side tests conducted as described below. Herbicidal data for the compounds of Examples 3-14 are given in Tables 6 and 7.

The plant species employed in these tests were selected from the following:

| Common Name (Abbrev.) | Scientific Name |
| --- | --- |
| Barnyardgrass (Barngr) | Echinochloa crus galli |
| Field Bindweed (Bindweed) | Convovulus arvensis |
| Blue Panicum (Blue Pan) | Panicum antidotale |
| Common Cocklebur (Coclebr) | Xanthium pensylvanicum |
| Field Corn (Corn) | Zea mays |
| Cotton | Gossypium hirsutum |
| Giant Foxtail (Giantfox) | Setaria faberi Herrm. |
| Green Foxtail (Greenfox) | Setaria viridis |
| Ivyleaf Morningglory (Ivyglory) | Ipomoea hederacea (L.) or Ipomoea lacumosa |
| Johnsongrass (Johngr) | Sorghum halepense |
| Rice | Oryza sativa |
| Hemp Sesbania (Sesbania) | Sesbania exaltata Raf. |
| Sicklepod (Sicklepd) | Cassia obtusifolia L. |
| Broadleaf Signalgrass (Signalgr) | Brachiaria platyphylla |
| Soybean | Glycine max |
| Velvetleaf (Velvetlf) | Abutilon theophrasti |
| Wheat | Triticum aestivum |
| Wild Mustard (Wmustard) | Brassica kaber |
| Yellow Nutsede (Yel Nuts) | Cyperus esculentus |
| Yellow Foxtail Yellowfox) | Setaria lutescens (Weigel) Hubb. |

Seeds or tubers of the plant test species were plant in furrows in steam sterilized sandy loam soil contained in disposable fiber flats. The flats had been filled to a depth of about 6.5 cm with the soil. A topping soil of equal portions of sand and sandy loam soil was placed uniformly on top of each flat to a depth of approximately 0.5 cm.

The flats for the preemergence tests were watered, then drenched with the appropriate amount of a solution of the test compound in a mixture of acetone and water containing a small amount (up to 0.5% v/v) of sorbitan monolaurate emulsifer/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence tests were placed in a greenhouse and watered for 8-10 days, then the foliage of the emerged test plants was sprayed with a solution of the test compound in acetone-water containing up to 0.5% sorbitan monolaurate. After spraying, the foliage was kept dry for 24 hours, then watered regularly for 21 days, and phytotoxicity data recorded.

Herbicidal data are given in Tables 1 and 2 below for the present compound of Example 2 (Compound 2) and for 1-(2,4-dichloro-5-propargyloxyphenyl)-3-methyl-4-difluoromethyl-Δ²-1,2,4-triazolin-5-one (Compound A). IN these tables "V" is vigor, "K" is % kill, and "kg/ha" is kilograms per hectare. Vigor ratings vary from 0 to 5 and have the following meaning:

V=5=no chemical injury; plants normal
4=slight injury; plants will or have already recovered
3=moderate injury; plants expected to recover
2=moderate to severe injury; plants are not expected to recover
1=severe injury; plants will not recover
0=dead plant

TABLE 1

Preemergence Activity

| | Rate of Application (kg/ha) | | | | | | | | | | | |
|---|---|---|---|---|---|---|---|---|---|---|---|---|
| | .5000 | | .2500 | | .1250 | | .0625 | | .0313 | | .0156 | |
| Species | V | K | V | K | V | K | V | K | V | K | V | K |
| Compound 2 | | | | | | | | | | | | |
| BARNGR | 0 | 100 | 0 | 100 | 0 | 100 | 0 | 100 | 0 | 100 | 0 | 100 |
| BINDWEED | 0 | 100 | 0 | 100 | 0 | 100 | 4 | 90 | 4 | 80 | 4 | 70 |
| BLUE PAN | 0 | 100 | 0 | 100 | 0 | 100 | 0 | 100 | 0 | 100 | 0 | 100 |
| COCKLEBR | 0 | 100 | 2 | 90 | 2 | 90 | 3 | 30 | 3 | 0 | 5 | 0 |
| CORN | 0 | 100 | 0 | 100 | 0 | 100 | 0 | 100 | 0 | 100 | 3 | 70 |
| COTTON | 3 | 80 | 3 | 80 | 4 | 30 | 4 | 0 | 5 | 0 | 4 | 0 |
| GIANTFOX | 0 | 100 | 0 | 100 | 0 | 100 | 0 | 100 | 0 | 100 | 0 | 100 |
| GREENFOX | 0 | 100 | 0 | 100 | 0 | 100 | 0 | 100 | 0 | 100 | 0 | 100 |
| IVYGLORY | 0 | 100 | 0 | 100 | 0 | 100 | 3 | 90 | 3 | 70 | 3 | 0 |
| JOHNGR | 0 | 100 | 0 | 100 | 0 | 100 | 0 | 100 | 0 | 100 | 0 | 100 |
| RICE | 0 | 100 | 0 | 100 | 0 | 100 | 0 | 100 | 2 | 90 | 3 | 40 |
| SESBANIA | 0 | 100 | 0 | 100 | 3 | 90 | 0 | 100 | 3 | 50 | 4 | 0 |
| SICKLEPD | 0 | 100 | 0 | 100 | 1 | 95 | 3 | 10 | 4 | 0 | 4 | 0 |
| SIGNALGR | 0 | 100 | 0 | 100 | 0 | 100 | 0 | 100 | 0 | 100 | 3 | 80 |
| SOYBEAN | 0 | 100 | 0 | 100 | 0 | 100 | 0 | 100 | 3 | 90 | 3 | 80 |
| VELVETLF | 0 | 100 | 0 | 100 | 0 | 100 | 0 | 100 | 0 | 100 | 0 | 100 |
| WHEAT | 0 | 100 | 0 | 100 | 0 | 100 | 2 | 80 | 3 | 20 | 3 | 20 |
| WMUSTARD | 0 | 100 | 0 | 100 | 0 | 100 | 0 | 100 | 4 | 50 | 5 | 0 |
| YEL NUTS | 0 | 100 | 2 | 60 | 2 | 70 | 3 | 60 | 3 | 10 | 4 | 0 |
| YELLOWFOX | 0 | 100 | 0 | 100 | 0 | 100 | 0 | 100 | 0 | 100 | 3 | 70 |
| Compound A* | | | | | | | | | | | | |
| BARNGR | 0 | 100 | 0 | 100 | 0 | 100 | 0 | 100 | 0 | 100 | 0 | 100 |
| BINDWEED | 0 | 100 | 0 | 100 | 4 | 0 | 4 | 0 | 5 | 0 | 5 | 0 |
| BLUE PAN | 0 | 100 | 0 | 100 | 0 | 100 | 0 | 100 | 0 | 100 | 0 | 100 |
| COCKLEBR | 3 | 90 | 3 | 80 | 4 | 80 | 4 | 80 | 5 | 0 | 5 | 0 |
| CORN | 0 | 100 | 0 | 100 | 0 | 100 | 0 | 100 | 2 | 70 | 2 | 70 |
| COTTON | 3 | 50 | 4 | 80 | 4 | 0 | 5 | 0 | 4 | 80 | 4 | 0 |
| GIANTFOX | 0 | 100 | 0 | 100 | 0 | 100 | 0 | 100 | 0 | 100 | 0 | 100 |
| GREENFOX | 0 | 100 | 0 | 100 | 0 | 100 | 0 | 100 | 0 | 100 | 0 | 100 |
| IVYGLORY | 0 | 100 | 0 | 100 | 3 | 50 | 4 | 0 | 4 | 0 | 5 | 0 |
| JOHNGR | 0 | 100 | 0 | 100 | 0 | 100 | 0 | 100 | 0 | 100 | 0 | 100 |
| RICE | 0 | 100 | 0 | 100 | 0 | 100 | 1 | 95 | 0 | 100 | 0 | 100 |
| SESBANIA | 0 | 100 | 0 | 100 | 3 | 90 | 0 | 100 | 3 | 30 | 4 | 0 |
| SICKLEPD | 2 | 90 | 3 | 0 | 4 | 0 | 4 | 0 | 4 | 0 | 4 | 0 |
| SIGNALGR | 0 | 100 | 0 | 100 | 0 | 100 | 0 | 100 | 0 | 100 | 0 | 100 |
| SOYBEAN | 0 | 100 | 0 | 100 | 2 | 90 | 3 | 80 | 4 | 60 | 4 | 0 |
| VELVETLF | 0 | 100 | 0 | 100 | 0 | 100 | 0 | 100 | 0 | 100 | 0 | 100 |
| WHEAT | 0 | 100 | 0 | 100 | 0 | 100 | 3 | 70 | 3 | 50 | 4 | 0 |
| WMUSTARD | 0 | 100 | 0 | 100 | 4 | 0 | 5 | 0 | 5 | 0 | 5 | 0 |
| YEL NUTS | 0 | 100 | 2 | 80 | 2 | 60 | 3 | 40 | 3 | 0 | 4 | 0 |
| YELLOWFOX | 0 | 100 | 0 | 100 | 0 | 100 | 0 | 100 | 0 | 100 | 3 | 95 |

*Compound A is 1-(2,4-dichloro-5-propargyloxyphenyl)-3-methyl-4-difluoromethyl-$\Delta^2$-1,2,4-triazolin-5-one.

TABLE 2

Postemergence Activity

| | Rate of Applications (kg/ha) | | | | | | | | | | | |
|---|---|---|---|---|---|---|---|---|---|---|---|---|
| | .5000 | | .2500 | | .1250 | | .0625 | | .0313 | | .0156 | |
| Species | V | K | V | K | V | K | V | K | V | K | V | K |
| Compound 2 | | | | | | | | | | | | |
| BARNGR | 0 | 100 | 0 | 100 | 0 | 100 | 0 | 100 | 0 | 100 | 3 | 80 |
| BINDWEED | 0 | 100 | 0 | 100 | 0 | 100 | 0 | 100 | 0 | 100 | 3 | 90 |
| BLUE PAN | 0 | 100 | 0 | 100 | 0 | 100 | 0 | 100 | 0 | 100 | 2 | 90 |
| COCKLEBR | 0 | 100 | 2 | 90 | 3 | 90 | 4 | 0 | 5 | 0 | 5 | 0 |
| CORN | 0 | 100 | 0 | 100 | 0 | 100 | 1 | 60 | 2 | 30 | 2 | 60 |
| COTTON | 0 | 100 | 0 | 100 | 0 | 100 | 3 | 90 | 0 | 100 | 1 | 90 |
| GIANTFOX | 0 | 100 | 0 | 100 | 0 | 100 | 0 | 100 | 0 | 100 | 0 | 100 |
| GREENFOX | 0 | 100 | 0 | 100 | 0 | 100 | 0 | 100 | 0 | 100 | 2 | 90 |
| IVYGLORY | 0 | 100 | 0 | 100 | 0 | 100 | 0 | 100 | 0 | 100 | 2 | 80 |
| JOHNGR | 0 | 100 | 0 | 100 | 0 | 100 | 0 | 100 | 4 | 30 | 3 | 60 |
| RICE | 0 | 100 | 0 | 100 | 0 | 100 | 0 | 100 | 1 | 90 | 3 | 70 |
| SESBANIA | 0 | 100 | 0 | 100 | 0 | 100 | 0 | 100 | 0 | 100 | 2 | 90 |
| SICKLEPD | 0 | 100 | 0 | 100 | 1 | 90 | 0 | 100 | 3 | 30 | 3 | 40 |
| SIGNALGR | 0 | 100 | 0 | 100 | 0 | 100 | 0 | 100 | 0 | 100 | 2 | 90 |
| SOYBEAN | 1 | 90 | 0 | 100 | 1 | 90 | 2 | 70 | 3 | 60 | 3 | 30 |
| VELVETLF | 0 | 100 | 0 | 100 | 0 | 100 | 0 | 100 | 0 | 100 | 0 | 100 |
| WHEAT | 0 | 100 | 0 | 100 | 0 | 100 | 2 | 70 | 4 | 30 | 5 | 0 |
| WMUSTARD | 0 | 100 | 0 | 100 | 0 | 100 | 0 | 100 | 3 | 70 | 5 | 0 |
| YEL NUTS | 2 | 80 | 0 | 100 | 2 | 60 | 2 | 20 | 3 | 0 | 5 | 0 |
| YELLOWFOX | 0 | 100 | 0 | 100 | 0 | 100 | 0 | 100 | 0 | 100 | 0 | 100 |
| Compound A* | | | | | | | | | | | | |
| BARNGR | 0 | 100 | 0 | 100 | 0 | 100 | 3 | 80 | 3 | 70 | 0 | 100 |

TABLE 2-continued

| | Postemergence Activity | | | | | | | | | | | |
|---|---|---|---|---|---|---|---|---|---|---|---|---|
| | Rate of Applications (kg/ha) | | | | | | | | | | | |
| | .5000 | | .2500 | | .1250 | | .0625 | | .0313 | | .0156 | |
| Species | V | K | V | K | V | K | V | K | V | K | V | K |
| BINDWEED | 0 | 100 | 0 | 100 | 0 | 100 | 4 | 60 | 4 | 0 | 0 | 100 |
| BLUE PAN | 0 | 100 | 0 | 100 | 0 | 100 | 0 | 100 | 0 | 100 | 0 | 100 |
| COCKLEBR | 2 | 0 | 3 | 0 | 4 | 0 | 3 | 0 | 5 | 0 | 5 | 0 |
| CORN | 0 | 100 | 0 | 100 | 0 | 100 | 2 | 90 | 4 | 0 | 4 | 60 |
| COTTON | 0 | 100 | 0 | 100 | 0 | 100 | 0 | 100 | 0 | 100 | 3 | 30 |
| GIANTFOX | 0 | 100 | 0 | 100 | 0 | 100 | 0 | 100 | 0 | 100 | 0 | 100 |
| GREENFOX | 0 | 100 | 0 | 100 | 0 | 100 | 0 | 100 | 0 | 100 | 0 | 100 |
| IVYGLORY | 0 | 100 | 0 | 100 | 0 | 100 | 1 | 90 | 1 | 90 | 4 | 90 |
| JOHNGR | 0 | 100 | 0 | 100 | 0 | 100 | 0 | 100 | 4 | 30 | 1 | 90 |
| RICE | 0 | 100 | 0 | 100 | 0 | 100 | 0 | 100 | 1 | 90 | 2 | 90 |
| SESBANIA | 0 | 100 | 0 | 100 | 0 | 100 | 0 | 100 | 0 | 100 | 2 | 90 |
| SICKLEPD | 0 | 100 | 0 | 100 | 0 | 100 | 5 | 0 | 4 | 80 | 5 | 0 |
| SIGNALGR | 0 | 100 | 0 | 100 | 0 | 100 | 0 | 100 | 0 | 100 | 0 | 100 |
| SOYBEAN | 2 | 90 | 2 | 80 | 3 | 40 | 3 | 30 | 4 | 0 | 4 | 0 |
| VELVETLF | 0 | 100 | 0 | 100 | 0 | 100 | 0 | 100 | 2 | 90 | 0 | 100 |
| WHEAT | 0 | 100 | 3 | 80 | 2 | 70 | 4 | 10 | 4 | 20 | 5 | 0 |
| WMUSTARD | 0 | 100 | 3 | 20 | 5 | 0 | 5 | 0 | 5 | 0 | 5 | 0 |
| YEL NUTS | 2 | 90 | 2 | 60 | 3 | 0 | 3 | 30 | 4 | 0 | 4 | 0 |
| YELLOWFOX | 0 | 100 | 0 | 100 | 0 | 100 | 0 | 100 | 0 | 100 | 4 | 70 |

*Compound A is 1-(2,4-dichloro-5-propargyloxyphenyl)-3-methyl-4-difluoromethyl-$\Delta^2$-1,2,4-triazolin-5-one.

In order to better compare herbicidal activity for the two test compounds, biological efficacy (BE) figures were calculated from percent kill and vigor using the equation $$BE = \%\ kill + X(100 - \%\ kill)$$

wherein X is a number assigned to the vigor rating according to the following schedule:

| vigor | X |
|---|---|
| 0 | 1 |
| 1 | 1 |
| 2 | 0.75 |
| 3 | 0.25 |
| 4 | 0.12 |
| 5 | 0 |

Tables 3 and 4 below show BE values calculated from the data in Tables 1 and 2 above for the present compound of Example 2 and the 2-chloro analog. BE values increase with herbicidal efficacy to a maximum value of 100.

TABLE 3

| | Preemergence Biological Efficacy (BE) | | | | | |
|---|---|---|---|---|---|---|
| | Rate of Application (kg/ha) | | | | | |
| | .5000 | .2500 | .1250 | .0625 | .0313 | .0156 |
| Species | BE | BE | BE | BE | BE | BE |
| | Compound 2 | | | | | |
| BARNGR | 100 | 100 | 100 | 100 | 100 | 100 |
| BINDWEED | 100 | 100 | 100 | 91 | 82 | 74 |
| BLUE PAN | 100 | 100 | 100 | 100 | 100 | 100 |
| COCKLEBR | 100 | 98 | 98 | 48 | 25 | 0 |
| CORN | 100 | 100 | 100 | 100 | 100 | 78 |
| COTTON | 85 | 85 | 38 | 12 | 0 | 12 |
| GIANTFOX | 100 | 100 | 100 | 100 | 100 | 100 |
| GREENFOX | 100 | 100 | 100 | 100 | 100 | 100 |
| IVYGLORY | 100 | 100 | 100 | 93 | 78 | 25 |
| JOHNGR | 100 | 100 | 100 | 100 | 100 | 100 |
| RICE | 100 | 100 | 100 | 100 | 98 | 55 |
| SESBANIA | 100 | 100 | 93 | 100 | 63 | 12 |
| SICKLEPD | 100 | 100 | 100 | 33 | 12 | 12 |
| SIGNALGR | 100 | 100 | 100 | 100 | 100 | 85 |
| SOYBEAN | 100 | 100 | 100 | 100 | 93 | 85 |
| VELVETLF | 100 | 100 | 100 | 100 | 100 | 100 |
| WHEAT | 100 | 100 | 100 | 95 | 40 | 40 |
| WMUSTARD | 100 | 100 | 100 | 100 | 56 | 0 |
| YEL NUTS | 100 | 90 | 93 | 70 | 33 | 12 |
| YELLOWFOX | 100 | 100 | 100 | 100 | 100 | 78 |
| | Compound A* | | | | | |
| BARNGR | 100 | 100 | 100 | 100 | 100 | 100 |
| BINDWEED | 100 | 100 | 12 | 12 | 0 | 0 |
| BLUE PAN | 100 | 100 | 100 | 100 | 100 | 100 |
| COCKLEBR | 93 | 85 | 82 | 82 | 0 | 0 |
| CORN | 100 | 100 | 100 | 100 | 93 | 93 |
| COTTON | 63 | 82 | 12 | 0 | 82 | 12 |
| GIANTFOX | 100 | 100 | 100 | 100 | 100 | 100 |
| GREENFOX | 100 | 100 | 100 | 100 | 100 | 100 |
| IVYGLORY | 100 | 100 | 63 | 12 | 12 | 0 |
| JOHNGR | 100 | 100 | 100 | 100 | 100 | 100 |
| RICE | 100 | 100 | 100 | 100 | 100 | 100 |
| SESBANIA | 100 | 100 | 93 | 100 | 48 | 12 |
| SICKLEPD | 98 | 25 | 12 | 12 | 12 | 12 |
| SIGNALGR | 100 | 100 | 100 | 100 | 100 | 100 |
| SOYBEAN | 100 | 100 | 98 | 85 | 65 | 12 |
| VELVETLF | 100 | 100 | 100 | 100 | 100 | 100 |
| WHEAT | 100 | 100 | 100 | 78 | 63 | 12 |
| WMUSTARD | 100 | 100 | 12 | 0 | 0 | 0 |
| YEL NUTS | 100 | 95 | 90 | 55 | 25 | 12 |
| YELLOWFOX | 100 | 100 | 100 | 100 | 100 | 96 |

*Compound A is 1-(2,4-dlchloro-5-propargyloxyphenyl)-3-methyl-4-difluoromethyl-$\Delta^2$-1,2,4-triazolin-5-one.

TABLE 4

| | Postemergence Biological Efficacy | | | | | |
|---|---|---|---|---|---|---|
| | Rate of Application (kg/ha) | | | | | |
| | .5000 | .2500 | .1250 | .0625 | .0313 | .0156 |
| Species | BE | BE | BE | BE | BE | BE |
| | Compound 2 | | | | | |
| BARNGR | 100 | 100 | 100 | 100 | 100 | 85 |
| BINDWEED | 100 | 100 | 100 | 100 | 100 | 93 |
| BLUE PAN | 100 | 100 | 100 | 100 | 100 | 98 |
| COCKLEBR | 100 | 98 | 93 | 12 | 0 | 0 |
| CORN | 100 | 100 | 100 | 100 | 83 | 90 |
| COTTON | 100 | 100 | 100 | 100 | 93 | 100 |
| GIANTFOX | 100 | 100 | 100 | 100 | 100 | 100 |
| GREENFOX | 100 | 100 | 100 | 100 | 100 | 98 |
| IVYGLORY | 100 | 100 | 100 | 100 | 100 | 95 |
| JOHNGR | 100 | 100 | 100 | 100 | 38 | 70 |
| RICE | 100 | 100 | 100 | 100 | 100 | 78 |

TABLE 4-continued

Postemergence Biological Efficacy

Rate of Application (kg/ha)

| Species | .5000 BE | .2500 BE | .1250 BE | .0625 BE | .0313 BE | .0156 BE |
|---|---|---|---|---|---|---|
| SESBANIA | 100 | 100 | 100 | 100 | 100 | 98 |
| SICKLEPD | 100 | 100 | 100 | 100 | 48 | 55 |
| SIGNALGR | 100 | 100 | 100 | 100 | 100 | 98 |
| SOYBEAN | 100 | 100 | 100 | 93 | 70 | 48 |
| VELVETLF | 100 | 100 | 100 | 100 | 100 | 100 |
| WHEAT | 100 | 100 | 100 | 93 | 38 | 0 |
| WMUSTARD | 100 | 100 | 100 | 100 | 78 | 0 |
| YEL NUTS | 95 | 100 | 90 | 80 | 25 | 0 |
| YELLOWFOX | 100 | 100 | 100 | 100 | 100 | 100 |
| Compound A* | | | | | | |
| BARNGR | 100 | 100 | 100 | 85 | 78 | 100 |
| BINDWEED | 100 | 100 | 100 | 65 | 12 | 100 |
| BLUE PAN | 100 | 100 | 100 | 100 | 100 | 100 |
| COCKLEBR | 75 | 25 | 12 | 25 | 0 | 0 |
| CORN | 100 | 100 | 100 | 98 | 12 | 65 |
| COTTON | 100 | 100 | 100 | 100 | 100 | 48 |
| GIANTFOX | 100 | 100 | 100 | 100 | 100 | 100 |
| GREENFOX | 100 | 100 | 100 | 100 | 100 | 100 |
| IVYGLORY | 100 | 100 | 100 | 100 | 100 | 91 |
| JOHNGR | 100 | 100 | 100 | 100 | 38 | 100 |
| RICE | 100 | 100 | 100 | 100 | 100 | 98 |
| SESBANIA | 100 | 100 | 100 | 100 | 100 | 98 |
| SICKLEPD | 100 | 100 | 100 | 0 | 82 | 0 |
| SIGNALGR | 100 | 100 | 100 | 100 | 100 | 100 |
| SOYBEAN | 98 | 95 | 55 | 48 | 12 | 12 |
| VELVETLF | 100 | 100 | 100 | 100 | 98 | 100 |
| WHEAT | 100 | 85 | 93 | 21 | 30 | 0 |
| WMUSTARD | 100 | 40 | 0 | 0 | 0 | 0 |
| YEL NUTS | 98 | 90 | 25 | 48 | 12 | 12 |
| YELLOWFOX | 100 | 100 | 100 | 100 | 100 | 74 |

*Compound A is 1-(2,4-dichloro-5-propargyloxyphenyl)-3-methyl-4-difluoromethyl-$\Delta^2$-1,2,4-triazolin-5-one.

Table 5 below shows a comparison of the average or overall biological efficacy for the present compound of Example 2 and the prior art compound against both weed grasses and weed broadleaves. The BE values for grasses represent the average of the BE values in Table 3 (preemergence) or Table 4 (postemergence) for barnyardgrass, blue panicum, giant foxtail, green foxtail, johnsongrass, signalgrass, yellow nutsedge, and yellow foxtail. The BE values for broadleaves represent the average for bindweed, cocklebur, ivyglory, sesbania, sicklepod, velvetleaf, and wild mustard. As can be seen from the table, both compounds performed equally well against the grasses, but the present compound was substantially more active against the more difficult to control broadleaves. In the preemergence tests against broadleaves, 0.5 kg/ha of the standard compound was needed for a BE of 99, whereas only 0.125 kg/ha of the present compound was required for the same level of control. Similarly, in the postemergence tests, 0.5 kg/ha of the standard gave a BE value of 96 while the present compound gave a BE of 99 at one-fourth the application rate, 0.125 kg/ha. Thus, in either preemergence or postemergence applications against the broadleaves, the present compound was about four times as active as the 2-chloro compound.

TABLE 5

Average Biological Efficacy

Rate of Application (kg/ha)

| Cpd. | Species | 0.50 BE | 0.25 BE | 0.125 BE | 0.0625 BE | 0.0313 BE | 0.0156 BE |
|---|---|---|---|---|---|---|---|
| | | Preemergence | | | | | |
| 2 | Grasses | 100 | 100 | 100 | 100 | 100 | 95 |
| | Broadleaves | 100 | 99 | 99 | 81 | 59 | 32 |
| A* | Grasses | 100 | 100 | 100 | 100 | 100 | 99 |
| | Broadleaves | 99 | 87 | 68 | 45 | 25 | 18 |
| | | Postemergence | | | | | |
| 2 | Grasses | 100 | 100 | 100 | 100 | 91 | 93 |
| | Broadleaves | 100 | 99 | 99 | 87 | 75 | 63 |
| A* | Grasses | 100 | 100 | 100 | 98 | 88 | 96 |
| | Broadleaves | 96 | 81 | 73 | 56 | 56 | 56 |

*Compound A is 2,4-dichloro-5-propargyloxyphenyl)-3-methyl-4-difluoromethyl-$\Delta^2$-1,2,4-triazolin-5-one.

For the compounds of Examples 3–4, phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The present rating system is as follows:

| Rating Percent Control | Description of Main Categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop injury no recovery | Moderate weed control |
| 70 | | Heavy injury and stand loss | Control somewhat less than satisfactory |
| 80 | Severe | Crop nearly destroyed a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for the compounds of Examples 3–14 in Tables 6 and 7 below. The test compounds are identified in the tables by Example numbers. In the tables "kg/ha" is kilograms per hectare and "% C" is percent control.

TABLE 6

Preemergence Activity

| Compound Number* | 3 | 4 | 5 | 6 | 7 | 8 | 9 | 10 | 11 | 12 | 13 | 14 |
|---|---|---|---|---|---|---|---|---|---|---|---|---|
| Rate (kg/ha) | 1.0 | 0.25 | 1.0 | 0.5 | 0.5 | 0.0625 | 0.0625 | 0.0625 | 0.0625 | 0.0625 | 0.0625 | 0.0625 |
| Species | % C | % C | % C | % C | % C | % C | % C | % C | % C | % C | % C | % C |
| Cotton | 50 | 70 | 100 | 20 | 90 | 0 | 0 | 10 | 0 | 0 | 10 | 20 |
| Soybean | 100 | 100 | 100 | 90 | 100 | 30 | 95 | 80 | 50 | 10 | 70 | 50 |
| Field Corn | 100 | 100 | 100 | 100 | 100 | 100 | 100 | 95 | 80 | 80 | 80 | 90 |
| Rice | 100 | 100 | 90 | 100 | 100 | 90 | 95 | 90 | 70 | 80 | 95 | 80 |

TABLE 6-continued

Preemergence Activity

| Compound Number* | 3 | 4 | 5 | 6 | 7 | 8 | 9 | 10 | 11 | 12 | 13 | 14 |
|---|---|---|---|---|---|---|---|---|---|---|---|---|
| Rate (kg/ha) | 1.0 | 0.25 | 1.0 | 0.5 | 0.5 | 0.0625 | 0.0625 | 0.0625 | 0.0625 | 0.0625 | 0.0625 | 0.0625 |
| Species | % C | % C | % C | % C | % C | % C | % C | % C | % C | % C | % C | % C |
| Wheat | 100 | 100 | 100 | 100 | 100 | 90 | 95 | 95 | 50 | 80 | 90 | 40 |
| Field Bindweed | 100 | 100 | 100 | 100 | 100 | — | 95 | — | — | — | 90 | — |
| Morningglory | 100 | 100 | 100 | 100 | 100 | 95 | 100 | 90 | 95 | 60 | 90 | 95 |
| Velvetleaf | 100 | 100 | 100 | 100 | 100 | 100 | 100 | 100 | 100 | 100 | 100 | 100 |
| Barnyardgrass | 100 | 100 | 100 | 100 | 100 | 100 | 100 | 100 | 100 | 80 | 100 | 95 |
| Green Foxtail | 100 | 100 | 100 | 100 | 100 | 90 | 100 | 100 | 100 | 90 | 100 | 100 |
| Johnsongrass | 100 | 100 | 100 | 100 | 100 | 90 | 95 | 100 | 100 | 90 | 100 | 90 |
| Yellow Nutsedge | 100 | 40 | 100 | 80 | 90 | 80 | — | 80 | 70 | 10 | — | 90 |

*The compound number is the number of the Example in which the particular compound was prepared.

TABLE 7

Postemergence Activity

| Compound Number* | 3 | 4 | 5 | 6 | 7 | 8 | 9 | 10 | 12 | 13 |
|---|---|---|---|---|---|---|---|---|---|---|
| Rate (kg/ha) | 1.0 | 0.25 | 1.0 | 0.5 | 0.5 | 0.125 | 0.0625 | 0.0625 | 0.125 | 0.125 |
| Species | % C | % C | % C | % C | % C | % C | % C | % C | % C | % C |
| Cotton | 100 | 100 | 100 | 100 | 100 | 70 | 80 | 50 | 80 | 80 |
| Soybean | 100 | 90 | 100 | 90 | 80 | 90 | 95 | 95 | 80 | 90 |
| Field Corn | 70 | 90 | 100 | 30 | 80 | 90 | 100 | 100 | 80 | 90 |
| Rice | 90 | 100 | 100 | 30 | 100 | 80 | 100 | 90 | 80 | 95 |
| Wheat | 60 | 100 | 100 | 30 | 90 | 80 | 95 | 50 | 50 | 95 |
| Field Bindweed | 100 | 100 | 100 | 100 | 100 | — | 100 | 95 | 90 | 100 |
| Morningglory | 100 | 100 | 100 | 100 | 100 | 100 | 100 | 100 | 80 | 100 |
| Velvetleaf | 100 | 100 | 100 | 100 | 100 | 100 | 100 | 100 | 100 | 100 |
| Barnyardgrass | 100 | 100 | 100 | 100 | 100 | 90 | 100 | 95 | 80 | 100 |
| Green Foxtail | 100 | 100 | 100 | 100 | 100 | 95 | 100 | 100 | 80 | 100 |
| Johnsongrass | 100 | 90 | 100 | 80 | 90 | 50 | 100 | 80 | 30 | 80 |
| Yellow Nutsedge | 100 | 50 | 100 | 40 | 90 | 80 | — | — | — | — |

*The compound number is the number of the Example in which the particular compound was prepared.

For herbicidal application, the active compounds as defined are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, water-soluble or water-dispersible granules, as powdery dusts, as wettable powders, emulsifiable concentrates, as solutions or as any of several other known types of formulations, depending on the desired mode of application.

For preemergence application these herbicidal compositions are usually applied either as sprays, dusts, or granules to the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic an inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing or emulsifying agents used in agricultural formulations include, for example, the alkyl and alkylaryl sulfonates and sulfates and their sodium salts; polyhydric alcohols; and other types of surface active agents, many of which are available in commerce. The surface active agent, when used, normally comprises 1% to 15% by weight of the herbicidal composition.

Other useful formulations for herbicidal applications include simple solutions of the active ingredient in a dispersant in which it is completely soluble at the desired concentration, such as acetone, alkylated naphthalenes, xylene or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersable granules are also useful formulations for herbicidal application of the present compounds. Such granular formulations are free-flowing, non-dusty, and readily water-soluble or or water-soluble or water-miscible. These soluble or dispersible granular formulations described in U.S. Pat. No. 3,920,442, incorporated herein by reference as useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metalachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazine-4-(3H)-one-2,2-dioxide (bentazon); triazine herbicides such as 6-chloro-N-ethyl-N-(1-methylethyl)-1,3,5-triazine-2,4-diamine (atrazine), and 2-4-chloro-6-(ethylamino)-1,3,5-triazin-2-ylamino-2-methyl-propanenitrile (cyanazine); dinitrolaniline herbicides such as 2,6-dinitro-N,N-dipropyl-4-(trifluoromethyl)-benzeneamine (trifluralin); and aryl urea herbicides such as N'-(3,4-dichlorophenyl)-N,N-dimethylurea (diuron) and N,N-dimethyl-N'-3-(trifluoromethyl)-phenylurea (fluometuron).

It is apparent that various modifications may be made in the formulation and application of the novel compounds of this invention, without departing from the inventive concepts herein, as defined in the following claims.

We claim:
1. The compound of the formula

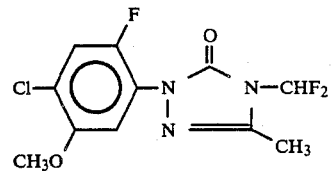

2. An herbicidal composition comprising an herbicidally effective amount of the compound of claim 1 in admixture with a suitable carrier.

3. A method for controlling undesired plant growth which comprises applying to the locus where control is desired an herbicidally effective amount of the composition of claim 2.

4. The method of claim 3 in which the composition is applied preemergently to the locus where control is desired and said locus is planted or to be planted with cotton.

* * * * *